US006793683B1

United States Patent
Laghi

(10) Patent No.: US 6,793,683 B1
(45) Date of Patent: Sep. 21, 2004

(54) PROSTHETIC FOOT WITH MEDIAL/LATERAL STABILIZATION

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

(21) Appl. No.: 10/064,847

(22) Filed: Aug. 22, 2002

(51) Int. Cl.[7] .................................................. A61F 2/66
(52) U.S. Cl. .............................. 623/52; 623/47; 623/53; 623/55
(58) Field of Search ............................... 623/53–56, 52, 623/47, 49

(56) References Cited

U.S. PATENT DOCUMENTS

| 4,645,509 | A | * | 2/1987 | Poggi et al. | 623/55 |
|---|---|---|---|---|---|
| 4,892,554 | A | * | 1/1990 | Robinson | 623/55 |
| 5,258,039 | A | * | 11/1993 | Goh et al. | 623/55 |
| 5,514,185 | A | * | 5/1996 | Phillips | 623/52 |
| 5,571,210 | A | * | 11/1996 | Lindh | 623/38 |
| 5,800,570 | A | * | 9/1998 | Collier | 623/55 |
| 6,254,643 | B1 | * | 7/2001 | Phillips | 623/52 |
| 6,402,790 | B1 | * | 6/2002 | Celebi | 623/38 |
| 6,443,995 | B1 | * | 9/2002 | Townsend et al. | 623/55 |
| 6,562,075 | B2 | * | 5/2003 | Townsend et al. | 623/38 |
| 6,602,295 | B1 | * | 8/2003 | Doddroe et al. | 623/55 |
| 2002/0087216 | A1 | * | 7/2002 | Atkinson et al. | 623/38 |

* cited by examiner

*Primary Examiner*—Alvin Stewart
(74) *Attorney, Agent, or Firm*—Ronald E. Smith; Smith & Hopen, P.A.

(57) ABSTRACT

A dynamic prosthetic foot provides medial and lateral stabilization. An ankle part diverges upwardly from a sole along a transverse parting line and includes a vertical part. A longitudinally extending slot divides the ankle part into a lateral and a medial ankle part and a pylon is connected to each of those parts. A plurality of parallel, equidistantly spaced, longitudinally extending slots are formed in the toe section and the heel section of the sole, respectively, to create a plurality of substantially independent toe and heel sections of narrow width. This enables the substantially independent toe and heel sections to respond independently to uneven terrain so that the user of the prosthetic foot is less likely to fall when ambulating over uneven terrain.

16 Claims, 4 Drawing Sheets

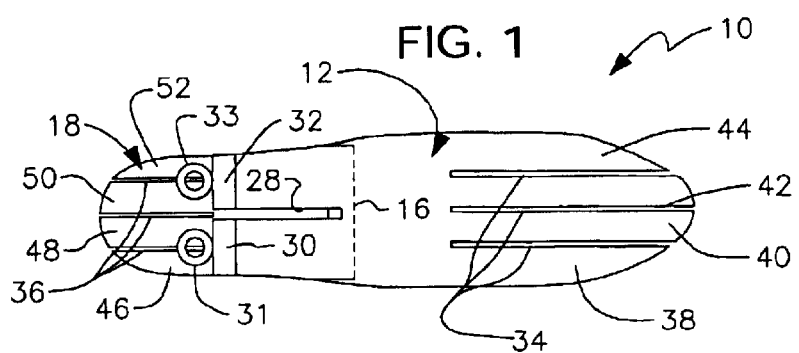
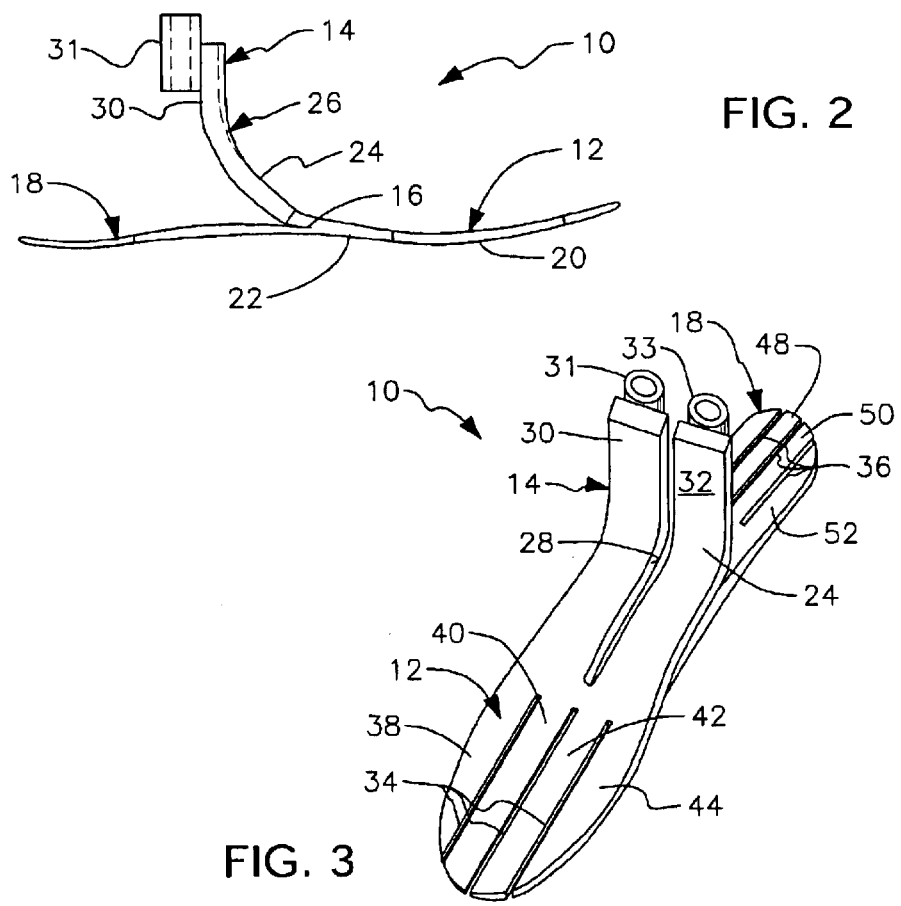

PROSTHETIC FOOT WITH MEDIAL/LATERAL STABILIZATION

BACKGROUND OF THE INVENTION

1. Field of the Invention

This invention relates generally, to the art of prosthetics. More particularly, it relates to improvements in prosthetic feet.

2. Description of the Prior Art

The prosthetic feet heretofore known are of rigid construction and are therefore of little utility on uneven terrain. Both the anterior and posterior sections of the foot are monolithic structures that cannot adapt to relatively small terrain features of the type that can cause a user to trip or fall.

There is a need, therefore, for a prosthetic foot that facilitates walking in uneven terrain.

However, in view of the prior art considered as a whole at the time the present invention was made, it was not obvious to those of ordinary skill in the pertinent art how the identified need could be fulfilled.

SUMMARY OF INVENTION

The long-standing but heretofore unfulfilled need for an improved dynamic prosthetic foot is now met by a new, useful, and nonobvious dynamic prosthetic foot having medial/lateral stabilization. The novel prosthetic foot includes a sole having an anterior, toe section and a posterior, heel section. An ankle part separates from the sole along a transverse parting line and includes a gradual upward bend and a vertically extending part.

At least one longitudinally extending slot is formed in the anterior section of the sole and divides the anterior section of the sole into at least two sections so that the at least two sections respond independently to uneven terrain. This enables a user of the prosthetic foot to ambulate across uneven terrain with less chance of falling as compared with a prosthetic foot lacking the at least one longitudinally extending slot.

At least one longitudinally extending slot is formed in the posterior section of the sole to divide the posterior section into at least two sections so that the at least two sections respond independently to uneven terrain. This enables a user of the prosthetic foot to ambulate across uneven terrain with less chance of falling as compared with a prosthetic foot lacking the at least one longitudinally extending slot dividing the posterior section.

A longitudinally extending slot divides the ankle part into a lateral pylon support and a medial pylon support. A lateral pylon connector is secured to a posterior side of the lateral pylon support and is adapted to securely engage a lateral pylon. A medial pylon connector is secured to a posterior side of the medial pylon support and is adapted to securely engage a medial pylon.

The lateral pylon support has a greater thickness and thus less resiliency than the medial pylon support so that externally imparted forces appearing on the lateral pylon support are transferred at least in part to the medial pylon support whereby a sound leg may oppose the transferred forces.

In a second embodiment, the lateral and medial pylon-supports and pylon connectors are supplanted by elongate lateral and medial pylons that are about twenty inches (20") in length. A prosthetist cuts the pylons as needed when fitting the novel foot to a prosthetic socket.

The elongate lateral and medial pylons are laminated at respective uppermost ends thereof to a prosthetic socket or are connected at respective uppermost ends thereof to a connector member that is laminated to the prosthetic socket.

Alternatively, the lateral and medial pylons are connected at respective uppermost ends thereof to a pyramid-receiving connector that engages a pyramid that depends from the prosthetic socket.

An important object of this invention is to provide a prosthetic foot having medial/lateral stabilization.

A more specific object is to provide a prosthetic foot having an anterior section and a posterior section that are adapted to facilitate ambulation on an uneven terrain.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a top plan view of a prosthetic foot with medial/lateral stabilization;

FIG. 2 is a side elevational view thereof;

FIG. 3 is a perspective view thereof;

DETAILED DESCRIPTION

Figure 4:
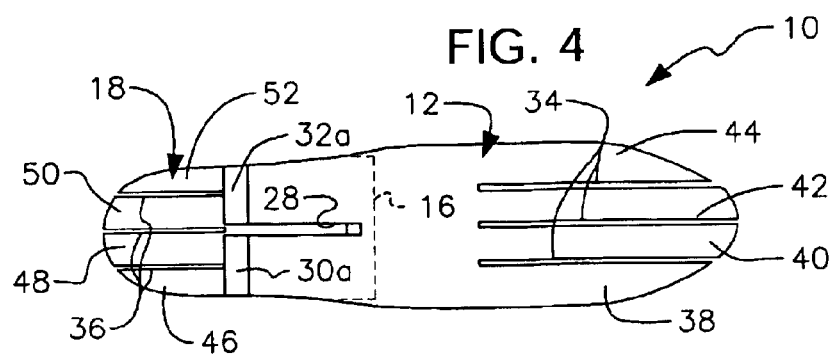
FIG. 4 is a top plan view of a second embodiment having elongate pylons.

Referring to FIGS. 1–3, it will there be seen that the reference numeral 10 denotes an illustrative embodiment of the novel dynamic prosthetic foot.

Prosthetic foot 10 includes a sole 12, an ankle part 14 that separates from sole 12 at transverse parting line 16, and a heel 18 that is formed integrally and is generally coplanar with sole 12. Transverse parting line 16 is about mid-length of foot 10, being a little closer to the heel/posterior end thereof than the toe/anterior end thereof.

Convexity 20 formed about mid-length of sole 12 performs a function corresponding to the ball of a natural foot.

Concavity 22 is formed about mid-length of foot 10 and performs a function corresponding to the arch of a natural foot.

Ankle part 14 includes a first upwardly-turned (with respect to sole 12) gradual bend 24 and vertically extending part generally denoted 26. A longitudinally extending slot 28 divides ankle part 14 into a lateral pylon support 30 and a medial pylon support 32. Slot 28 extends from a free end of ankle part 14 to a point slightly anterior to transverse parting line 16.

A lateral pylon, not shown, is secured by pylon connector 31 to a trailing side of lateral pylon support 30 and a medial pylon, not shown, is secured by pylon connector 33 to a trailing side of medial pylon support 32.

Lateral pylon support 30 is a little thicker and thus less flexible than medial pylon support 32 as indicated in all three Figures, with the desirable result that externally imparted forces are transferred from the lateral side of prosthetic foot 10 to the medial side thereof as is the case in a natural foot. This directs such forces toward the natural leg of the prosthetic foot user, as is desirable.

A first plurality of longitudinally extending slots, collectively denoted 34, are formed in the anterior, toe section of sole 12. Each slot 34 extends form the toe end of the sole to a location that is on the anterior side of transverse parting line 16. Slots 34 are parallel to a longitudinal axis of sole 12 and are thus parallel to the direction of travel. Moreover, slots 34 are equidistantly spaced a part from one another.

Similarly, a second plurality of longitudinally extending slots, collectively denoted 36, are formed in the posterior section of heel 18. Slots 36 are parallel to a longitudinal axis of sole 12 and are thus also parallel to the direction of travel. Moreover, slots 36 are also equidistantly spaced apart from one another.

Each slot 36 extends from the heel end of the sole to a location that is substantially coincident with a vertical plane that cuts through sole 12 at the trailing/heel side of lateral pylon support 30 and medial pylon support 32.

The number and spacing of slots 34, 36, is not highly critical, but the number and spacing depicted is believed to be optimal.

Anterior slots 34 enable sole sections 38, 40, 42, and 44 to respond individually to bumps and depressions in terrain. Posterior slots 36 enable heel sections 46, 48, 50, and 52 to do the same. The user is therefore better able to ambulate on uneven terrain because the sole and heel sections of foot 10 do not respond monolithically to the terrain as in the prosthetic feet of the prior art.

Figure 5:
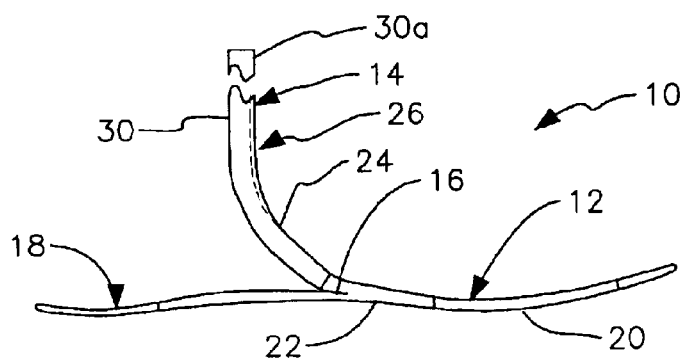
FIG. 5 is a side elevational view of the FIG. 4 second embodiment.
Figure 6:
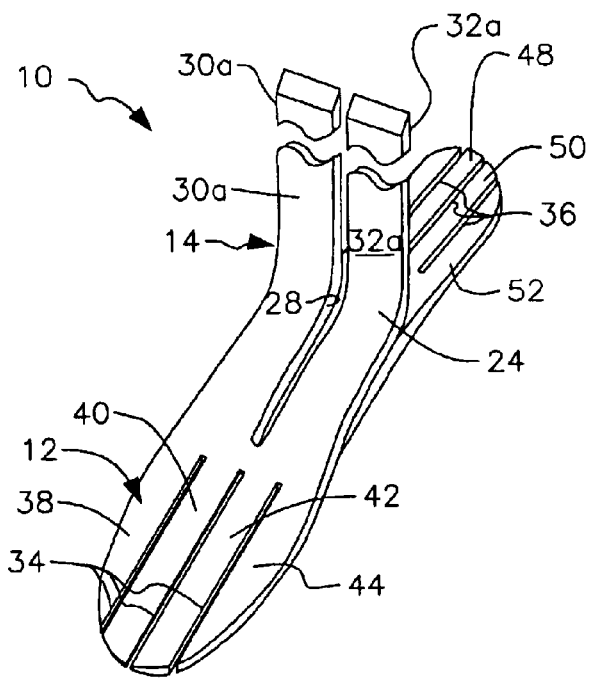
FIG. 6 is a perspective view of the FIG. 4 embodiment.

A second embodiment, depicted in FIGS. 4–6, has the same advantages as the first embodiment, but advantageously obviates pylon connectors 31 and 33. Pylon supports 30 and 32 are elongated to an extent of about twenty inches (20") and thus serve as lateral and medial pylons, 30a, 32a, respectively. A prosthetist cuts pylons 30a, 32a as needed when novel foot 10 is fitted to a residual limb.

Figure 7:
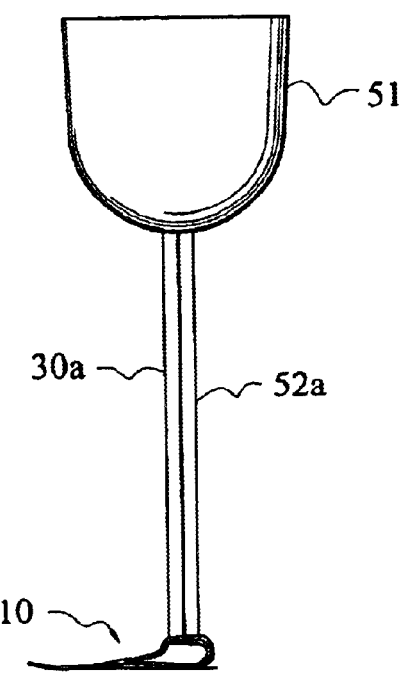
FIG. 7 is a perspective view of the elongate pylons embodiment when attached to a socket.

FIG. 7 depicts the novel structure when equipped with elongate pylons 30a, 32a.

After pylons 30a, 32a have been cut to a desired length, the prosthetist has several options by which the pylons may be connected to prosthetic socket 54. Pylons 30a, 32a may be laminated into prosthetic socket 54 as illustrated in said FIG. 7. This forms a permanent connection between pylons 30a, 32a and socket 54.

Figure 8:
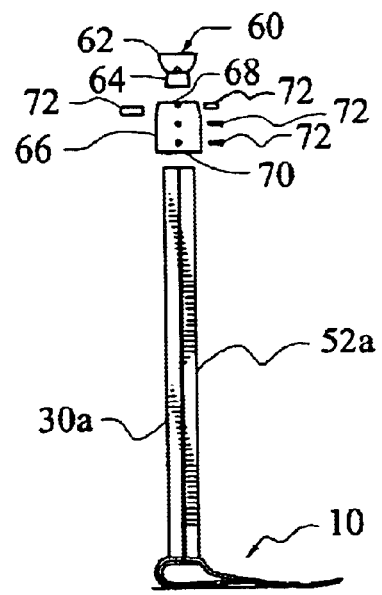
FIG. 8 is a perspective view of the elongate pylons embodiment and further depicting connector means, in exploded form, for connecting said elongate pylons to a socket.

A second option includes the use of a commercially available pyramid connector 60 as depicted in FIG. 8. Such pyramid connectors have been in use for fifty or so years. Pyramid connector 60 includes upper part 62 and lower part 64 that depends from the upper part. Upper part 62 is attached to the lowermost or distal end of socket 54. A hollow pyramid-receiving connector 66 has an open upper end 68 that receives lower part 64 of pyramid connector 60 and an open lower end 70 that receives the respective uppermost ends of pylons 30a, 32a. Lower end 64 of pyramid connector 60 and the respective upper ends of pylons 30a, 32a are captured in said hollow pyramid-receiving connector 66 by a plurality of set screws and other suitable fastening means, collectively denoted 72.

Pyramid connector 62 and pyramid-receiving connector 66 are employed to enable adjustment of the angle of pylons 30a, 32a so that prosthetic foot 10 falls in the correct medial/lateral and anterior/posterior planes, as perhaps best understood by making reference to FIGS. 7 and 8.

A third option available to the prosthetist after cutting pylons 30a, 32a to their correct length is to laminate the pylons to an unillustrated component and to attach that component to the socket.

Figure 9A:
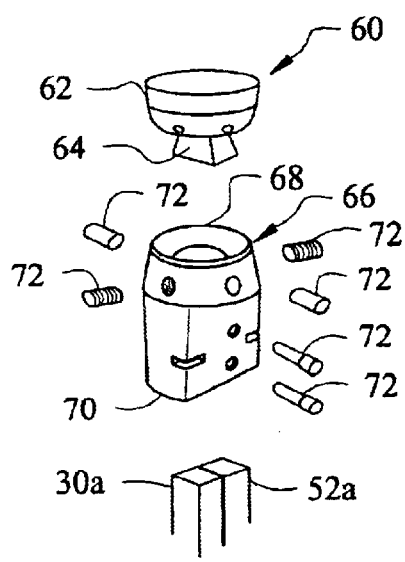
FIG. 9A is an exploded first perspective view of said connector means.
Figure 9B:
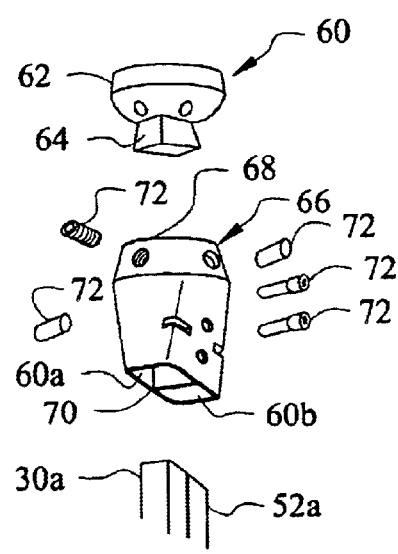
FIG. 9 is an exploded second perspective view of said connector means.
FIG. 9C is a first perspective view of a pyramid-receiving connector.
FIG. 9D is a second perspective view of said pyramid-receiving connector.
Figure 9C:
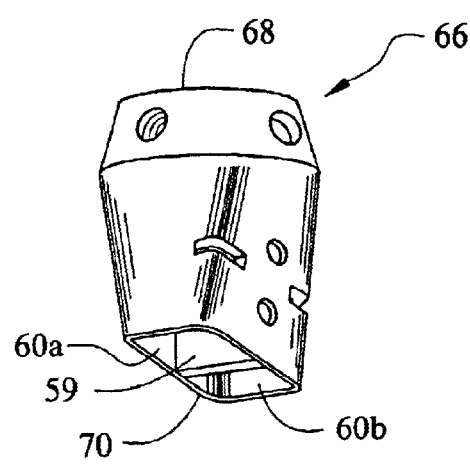
Figure 9D:
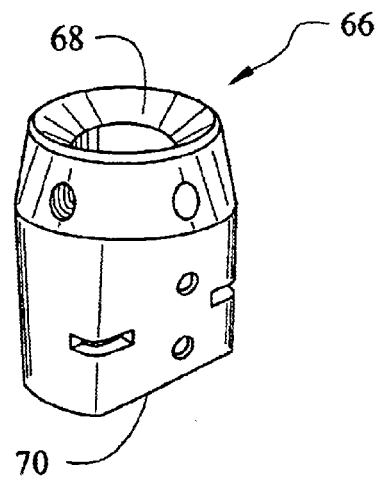

FIGS. 9A and 9B provide a more detailed perspective view of pyramid connector 60 and pyramid-receiving connector 66. FIGS. 9C and 9D provide a more detailed perspective view of pyramid-receiving connector 66.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:
1. A dynamic prosthetic foot, comprising:
   a sole having an anterior, toe section and a posterior, heel section;
   an ankle part that separates from said sole along a transverse parting line;
   said ankle part including a gradual upward bend and a vertically extending part;
   at least one longitudinally extending slot formed in said anterior section of said sole;
   said at least one longitudinally extending slot dividing said anterior section of said sole into at least two sections so that said at least two sections respond independently to uneven terrain;
   at least one longitudinally extending slot dividing said posterior section of said sole into at least two sections so that said at least two sections respond independently to uneven terrain;
   a longitudinally extending slot that divides said ankle part into a lateral pylon support and a medial pylon support;
   said longitudinally extending slot that divides said ankle part being separate from said at least one longitudinally extending slot that divides said anterior section of said sole;
   whereby a user of said prosthetic foot is able to ambulate across uneven terrain with less chance of falling as compared with a prosthetic foot lacking said at least one longitudinally extending slot.

2. The dynamic prosthetic foot of claim 1, further comprising:
a lateral pylon connector secured to a trailing side of said lateral pylon support.

3. The dynamic prosthetic foot of claim 1, further comprising:
a medial pylon connector secured to a trailing side of said medial pylon support.

4. The dynamic prosthetic foot of claim 1, wherein said lateral pylon support has a greater thickness and thus less resiliency than said medial pylon support so that externally imparted forces appearing on said lateral pylon support are transferred at least in part to said medial pylon support whereby a sound leg may oppose said transferred forces.

5. The dynamic prosthetic foot of claim 1, wherein said transverse parting line is approximately half way between a toe end of said sole and a heel end of said sole.

6. The dynamic prosthetic foot of claim 1, further comprising:
a convexity formed about mid-length of said sole to perform the function of a ball of a natural foot.

7. The dynamic prosthetic foot of claim 1, further comprising:
a concavity formed about mid-length of said prosthetic foot to perform the function of an arch of a natural foot.

8. A dynamic prosthetic foot, comprising:
a sole having an anterior, toe section and a posterior, heel section;
an ankle part that separates from said sole along a transverse parting line;
said ankle part including a gradual upward bend and a vertically extending part;
at least one longitudinally extending slot formed in said anterior section of said sole;
at least one longitudinally extending slot dividing said posterior, heel section of said sole into at least two sections so that said at least two sections respond independently to uneven terrain;
a longitudinally extending slot that divides said ankle part into a lateral pylon and a medial pylon;
said longitudinally extending slot that divides said ankle part being separate from said longitudinally extending slot formed in said anterior section of said sole;
said lateral pylon and said medial pylon each being adapted to be engaged at their respective uppermost ends to a prosthetic socket;
whereby a user of said prosthetic foot is able to ambulate across uneven terrain with less chance of falling as compared with a prosthetic foot lacking said at least one longitudinally extending slot that divides said posterior, heel section of said sole; and
whereby said lateral and medial pylons are adapted to be cut to a preselected length when said dynamic prosthetic foot is fitted to a residual limb.

9. The dynamic prosthetic foot of claim 8, further comprising:
said at least one longitudinally extending slot dividing said anterior section of said sole into at least two sections so that said at least two sections respond independently to uneven terrain;
whereby a user of said prosthetic foot is able to ambulate across uneven terrain with less chance of falling as compared with a prosthetic foot lacking said at least one longitudinally extending slot that divides said anterior section of said sole.

10. The dynamic prosthetic foot of claim 8, wherein said lateral pylon has a greater thickness and thus less resiliency than said medial pylon so that externally imparted forces appearing on said lateral pylon are transferred at least in part to said medial pylon whereby a sound leg may oppose said transferred forces.

11. The dynamic prosthetic foot of claim 8, wherein said transverse parting line is approximately half way between a toe end of said sole and a heel end of said sole.

12. The dynamic prosthetic foot of claim 8, further comprising:
a concavity formed about mid-length of said prosthetic foot to perform the function of an arch of a natural foot.

13. The dynamic prosthetic foot of claim 8, further comprising:
a convexity formed about mid-way between said concavity and said toe end of said sole, said convexity performing the function of a ball of a natural foot.

14. The dynamic prosthetic foot of claim 8, wherein said lateral and medial pylons are laminated at respective uppermost ends thereof to a prosthetic socket.

15. The dynamic prosthetic foot of claim 8, wherein said lateral and medial pylons are connected at respective uppermost ends thereof to a connector member and wherein said connector member is laminated to a prosthetic socket.

16. The dynamic prosthetic foot of claim 8, wherein said lateral and medial pylons are connected at respective uppermost ends thereof to a pyramid-receiving connector that engages a pyramid that depends from said prosthetic socket.

* * * * *